United States Patent
Karsten et al.

(12) 
(10) Patent No.: US 7,342,094 B1
(45) Date of Patent: Mar. 11, 2008

(54) TUMOR VACCINES FOR MUC1-POSITIVE CARCINOMAS

(75) Inventors: Uwe Karsten, Berlin (DE); Franz-Georg Hanisch, Köln (DE); Hans Paulsen, Hamburg (DE)

(73) Assignee: Max-Delbrück-Centrum für Molekulare Medizin, Berlin (DE)

( * ) Notice: Subject to any disclaimer, the term of this patent is extended or adjusted under 35 U.S.C. 154(b) by 612 days.

(21) Appl. No.: 09/606,910

(22) Filed: Jun. 29, 2000

Related U.S. Application Data

(63) Continuation of application No. PCT/DE98/03819, filed on Dec. 30, 1998.

(30) Foreign Application Priority Data

Dec. 30, 1997 (DE) ................................ 197 58 400

(51) Int. Cl.
*A61K 38/00* (2006.01)
(52) U.S. Cl. .......................................... 530/326; 514/13
(58) Field of Classification Search ............... 435/7.23; 424/185.1, 193.1, 194.1, 198.1, 277.1; 536/123, 536/123.1; 530/355, 300, 350, 326; 514/2, 514/16, 13
See application file for complete search history.

(56) References Cited

U.S. PATENT DOCUMENTS 5,989,552 A * 11/1999 McKenzie et al.
6,465,220 B1 * 10/2002 Hassan et al. ................ 435/97

FOREIGN PATENT DOCUMENTS

GB WO-90/05142 * 5/1990
WO WO 88/05054 7/1988

OTHER PUBLICATIONS

Osband et al, Immunology Today, 1990, vol. 11, p. 193-195.*
Hanisch et al (Cancer Res., 1995, vol. 55(18):4036-40, abstract).*
Skolnick J, et al. Trends Biotechnol Jan. 2000; 18 (1): 34-9.*
Bowie JU, et al. Science Mar. 16, 1990; 247 (4948): 1306-10.*
Yamshchikov G, et al. Clin Cancer Res. Mar. 2001; 7 (3 Suppl): 909s-916s.*
Bocchia M, et al. Haematologica. Nov. 2000; 85(11): 1172-206.*
Bodey B, et al. Anticancer Res. Jul.-Aug. 2000;20 (4): 2665-76.*
Ezzell C. J NIH Res. Jan. 1995; 7: 46-9.*
Splitler LE. Cancer Biotherapy, 1995; 10 (1): 1-3.*
Lee KH, et al. J Immunol. Dec. 1, 1999; 163 (11): 6292-300.*
Boon, T. Adv Cancer Res. 1992; 58: 177-210.*
Zaks TZ, et al., Cancer Res. Nov. 1, 1998; 58 (21): 4902-8.*
Gao P, et al., J Immunother. Nov.-Dec. 2000; 23 (6): 643-53.*
Gura T. Science. Nov. 7, 1997; 278 (5340): 1041-2.*
Lu J, et al. Cancer Res. Oct. 15, 2002; 62 (20): 5807-12.*
Karsten U, et al., Cancer Res. Jun. 15, 1998; 58 (12): 2541-9.*

* cited by examiner

*Primary Examiner*—Stephen L. Rawlings
(74) *Attorney, Agent, or Firm*—Duane A. Stewart, III; Buchanan Ingersoll & Rooney PC

(57) ABSTRACT

Tumor vaccines for the use against MUC1 positive carcinomas are presented. A tumor vaccine containing synthetic peptides comprising sequences of the human epithelial mucin MUC1 containing the immunodominat region PDTR-PAP which is glycosylated at the threonine. Preferred glycosylation of the immunodominant region is a O-glycosidically linked a-N-acetylgalactosamine (GalNAc) or short chained oligosaccharides. The present invention can be used on all MUC1-positive carcinomas.

10 Claims, 1 Drawing Sheet

US 7,342,094 B1

TUMOR VACCINES FOR MUC1-POSITIVE CARCINOMAS

CROSS-REFERENCE TO RELATED APPLICATIONS

This is a continuation of our copending application PCT DE98/03819, filed Dec. 30, 1998.

FIELD OF INVENTION

The invention relates to tumor vaccines of a new type, based on the molecular structure of human epithelial mucin (MUC1). The invention can be used for the immunotherapy of carcinomas.

BACKGROUND

Epithelial mucins are glycoproteins with repetitive amino acid sequences and a high proportion of carbohydrates which are partially bound to membranes, partially secreted and are to be found on many glandular epithelia. The epithelial mucin known best is the membrane-bound MUC1, described also as PEM, PUM, EMA, MAM-6, PAS-0 or episialine (Finn, O. et al., Immunol. Reviews 145:61, 1995) the extracellular part of which consists of a variable number of repeating units of 20 amino acids, the so-called tandem repeats. The MUC1 is not a tumor specific molecule per se; its suitability as tumor antigen is based on the fact that its carbohydrate portion is qualitatively and quantitatively changed in tumors (Burchell, J. and Taylor-Papadimitriou, J., Epith. Cell Biol. 2:155, 1993). Here, new epitopes appear which are detected by the immune system (humoral and cellular defense).

After operatively removing the primary tumor (or after a radiation or chemotherapy) one, as a rule, has to proceed on the assumption that tumor cells still remain in the body (minimal residual disease). These tumor cells which represent a potential danger, are combated by various endogenic mechanisms the efficiency of which may be intensified by an adjuvant immunotherapy. The most effective adjuvant immunotherapy is vaccination. Here, two prerequisites are present: first, a suitable target antigen (epitope) has to be present on the tumor cells, and second that it should be possible to prepare a form of vaccine that is immunogenically as strong as possible, most suitably in a synthetic form.

Non-glycosylated oligo-repeat peptides of MUC1 represent a suitable target antigen in a number of frequently occurring carcinomas (Apostolopoulos, V. and McKenzie, I. F. C., Crit. Rev. Immunol. 14:293, 1994). The immunodominant region of MUC1 is the PDTRPAP motif which occurs on each tandem repeat. However, experiments carried out so far to develop a vaccine on the basis of an individual tandem repeat have not been successful. According to the present state of knowledge a minimum length of the peptide which will be reached only in 3-5 tandem repeats is required for achieving the immunogenic conformation of the peptide (Fontenot, J. D. et al., J. Biomol. Struct. Dyn. 13:245, 1995).

BRIEF DESCRIPTION OF THE DRAWING

The invention is described with reference to the drawing wherein.

DESCRIPTION OF THE INVENTION

Figure 1:
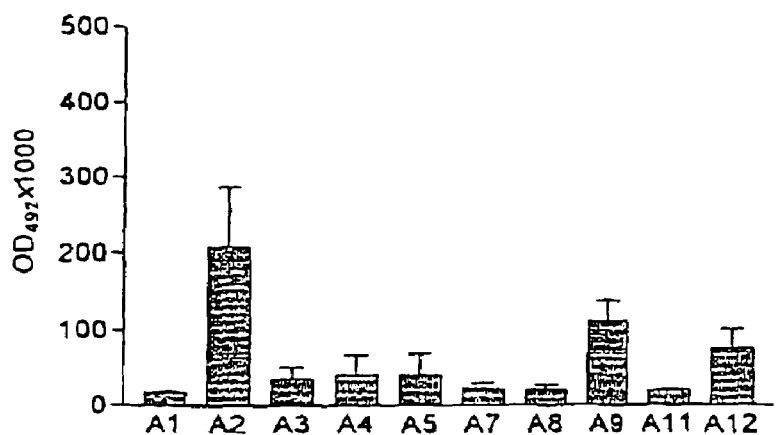
FIG. 1 shows bending of the anti-MUC1-antibody A76-A/C7 on the glycopeptides A1-A9 and A11-A12.
Figure 2:
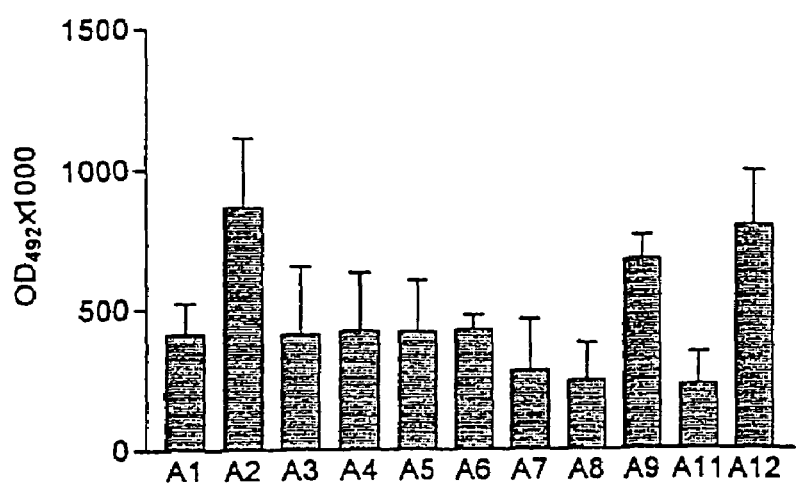
FIG. 2 shows bending of the anti-MUC1-antibody MFO6 on the glycopeptides A9 and A11-15, A12.

It is an object of the present invention to develop tumor vaccines on the basis of the molecular structure of human epithelial mucin MUC1 for combating tumor cells which remain in the body after other therapies.

In the immunological investigation of synthetic glycopeptides which correspond to a tandem repeat of the MUC1 there it was surprisingly detected that the glycosylation of threonine in the immunodominant PDTRPAP (SEQ. ID NO: 1) region with α-GalNAc significantly increases the antigenicity. So far we proceeded on the theory that this position is not glycosylated in native MUC1, because it was assumed previously that, as a rule, glycosylation hindered the identification of peptide epitopes and the results of in vitro glycosylation experiments (Stadie. T. et el., Eur. J. Biochem. 229:140 (1995). Latest investigations (Mueller, S., et el., J. Biol. Chem. 272:24780, 1997), however, showed that threonine may be well glycosylated in vivo in the PDTRPAP (SEQ. ID NO: 1) variant. From these latest results the conclusion was drawn that the antigenicity (and in this connection also the immunogenicity) of the MUC1 tandem repeat will be significantly increased by glycosylating threonine in the PDTRPAP (SEQ. ID NO: 3) variant by means of GalNAc or by a short oligosaccharide. Thus, the immunogenic conformation of the immunodominant region is already reached by an individual tandem repeat. The antigenicity of the glycosylated PDTRPAP (SEQ. ID NO: 1) variant in a monorepeat exceeds even that of the oligomeric non-glycosylated peptide.

This discovery develops tumor vaccine mostly but not exclusively from human epithelial mucin MUC1 various molecular sizes glycosylated on threonine of the PDTRPAP (SEQ. ID NO: 1) variant by GalNAc, or a short oligosaccharide. That objective is met by synthetic peptides of various lengths, suitably a synthetic peptide having a length of at least 20 amino acids, and modified by human epithelial MUC1 glycosylated threonine and containing the immunodominant PDTRPAP (SEQ. ID NO: 1) region. The glycosylation can be suitably carried out by a monosaccharide, acetylgalactosamine (GalNAc), a short-chained oligosaccharide, and the disaccharide GalB-1,3GalNAc.

The tumor vaccine of the present invention can be suitably administered to a patient against mammary, colorectal or pancreatic carcinomas.

The invention is explained in greater detail by reference to the following example.

EXAMPLE

Antigenicity of Synthetic, MUC1-Derived Glycopeptides

In the following experiment, the binding is investigated of monoclonal antibodies against the immunodominant PDTRPAP (SEQ. ID NO: 1) variant of the epithelial mucin to synthetic glycopeptides of this mucin in a solid-phase immunoassay (ELISA). The glycopeptides marked as A1 to A12 are indicated in the following Table. They correspond to an overlapping tandem repeat of MUC1 and contain 5 potential glycosylating sites (3× threonine, 2× serine); A1-A9 contains an additional alanine. The glycopeptides differ by the number and position of the glycosylating sites as specified in the Table. A1-A9 carry the Thomsen-Friedenreich (TF)

antigen as glycan β-D-Gal(1-3)α-D-GalNAc—O—R whereas A11 and A12 carry only α-GalNAc—O—R (the Tn antigen). The antibodies used are: A76-A/C7 (mouse, IgG1, epitope: APDTRPAP (SEQ. ID NO: 2)) and MFO6 (mouse, IgG1, epitope: DTRPAP (SEQ. ID NO: 3)) (see: Rye, P. D., Price, M. R., eds., ISOBM TD-4 International Workshop on Monoclonal Antibodies against MUC1, Tumor Biol. 19, Suppl. 1, 1998).

TABLE

Synthetic glycopeptides;
the peptide corresponds to the basic
structure of the epithelial mucin (MUC1).
The immunodominant region is underlined as also shown in the drawing.

A: Glycosylation with TF:

(SEQ. ID NO.: 4)
A--H--G--V--T--S--A--P--D--T--R--P--A--P--G--S--T--A--P--P--A
1  2  3  4  5  6  7  8  9  10 11 12 13 14 15 16 17 18 19 20 21
Peptide # glycosylated in position:
A1   5
A2   10
A3   17
A4   6
A5   16
A6   5, 17
A7   5, 16, 17
A8   5, 6, 16, 17
A9   5, 6, 10, 16, 17

TABLE-continued

Synthetic glycopeptides;
the peptide corresponds to the basic
structure of the epithelial mucin (MUC1).
The immunodominant region is underlined as also shown in the drawing.

B: Glycosylation with Tn:

(SEQ. ID NO.:5)
H--G--V--T--S--A--P--D--T--R--P--A--P--G--S--T--A--P--P--A
2  3  4  5  6  7  8  9  10 11 12 13 14 15 16 17 18 19 20 21
Peptide # glycosylated in position:
A11   5, 17
A12   5, 6, 10, 16, 17

The results show that the peptides glycosylated in position 10 with the two antibodies shown in the example bind significantly stronger than peptides not glycosylated in this position. Glycosylations in other positions have no influence. Substitution by Tn or TF is equal. The binding behavior demonstrated in this example is also shown by other MUC1 antibodies; yet, there are also exceptions. The increased antigenicity of the peptides glycosylated in position 10 can also be shown in inhibition experiments.

The results show that a glycosylation of the immunodominant region of the MUC1 peptide by means of Tn or TF significantly increases the antigenicity.

The invention claimed is:

1. A synthetic peptide consisting of: (a) the amino acid sequence of SEQ ID NO: 4, wherein the sequence PDTRPAP (SEQ ID NO: 1) is glycosylated at the threonine residue; or (b) the amino acid sequence of SEQ ID NO: 5, wherein said the sequence PDTRPAP (SEQ. ID NO: 1) is glycosylated at the threonine residue.

2. The synthetic peptide of claim 1, wherein the glycosylation of the threonine of the PDTRPAP (SEQ ID NO: 1) is a monosaccharide.

3. The synthetic peptide of claim 1, wherein the glycosylation of the threonine of the PDTRPAP (SEQ ID NO: 1) is a α-N-acetylgalactosamine (GalNAc).

4. The synthetic peptide of claim 1, wherein the glycosylation of the threonine of the PDTRPAP (SEQ ID NO: 1) is a short-chained oligosaccharide.

5. The synthetic peptide of claim 1, wherein the glycosylation of the threonine of the PDTRPAP (SEQ ID NO: 1) is the disaccharide Galβ-1,3GalNAc.

6. A synthetic peptide consisting of: (a) at least one tandem repeat of the amino acid sequence of SEQ ID NO: 4, wherein of the sequence PDTRPAP (SEQ ID NO: 1) is glycosylated at the threonine residue; or (b) at least one tandem repeat of the amino acid sequence of SEQ ID NO: 5 wherein the sequence PDTRPAP (SEQ ID NO: 1) is glycosylated at the threonine residue.

7. The synthetic peptide of claim 6, wherein the glycosylation of the threonine of each PDTRPAP (SEQ ID NO: 1) is a monosaccharide.

8. The synthetic peptide of claim 6, wherein the glycosylation of the threonine of each PDTRPAP (SEQ ID NO: 1) is a α-N-acetylgalactosamine (GalNAc).

9. The synthetic peptide of claim 6, wherein the glycosylation of the threonine of each PDTRPAP (SEQ ID NO: 1) is a short-chained oligosaccharide.

10. The synthetic peptide of claim 6, wherein the glycosylation of the threonine of each PDTRPAP (SEQ ID NO: 1) is the disaccharide Galβ-1,3GalNAc.

* * * * *

UNITED STATES PATENT AND TRADEMARK OFFICE
CERTIFICATE OF CORRECTION

PATENT NO.        : 7,342,094 B1                                          Page 1 of 1
APPLICATION NO.   : 09/606910
DATED             : March 11, 2008
INVENTOR(S)       : Uwe Karsten, Franz-Georg Hanisch and Hans Paulsen It is certified that error appears in the above-identified patent and that said Letters Patent is hereby corrected as shown below:

On title page at Item (30), Foreign Application Priority Data, change the German application number "197 58 400" to --197 58 400.4--

Signed and Sealed this

Thirtieth Day of September, 2008

JON W. DUDAS
*Director of the United States Patent and Trademark Office*

SEQUENCE LISTING

```
<160> NUMBER OF SEQ ID NOS: 6

<210> SEQ ID NO 1
<211> LENGTH: 7
<212> TYPE: PRT
<213> ORGANISM: human
<220> FEATURE:
<221> NAME/KEY: DOMAIN
<222> LOCATION: (1) .. (7)
<223> OTHER INFORMATION: immunodominant region of MUC1

<400> SEQUENCE: 1

Pro Asp Thr Arg Pro Ala Pro
1               5

<210> SEQ ID NO 2
<211> LENGTH: 8
<212> TYPE: PRT
<213> ORGANISM: mouse
<220> FEATURE:
<221> NAME/KEY: DOMAIN
<222> LOCATION: (1) .. (8)
<223> OTHER INFORMATION: A76-A/C7 epitope

<400> SEQUENCE: 2

Ala Pro Asp Thr Arg Pro Ala Pro
1               5
```

```
<210> SEQ ID NO 3
<211> LENGTH: 6
<212> TYPE: PRT
<213> ORGANISM: mouse
<220> FEATURE:
<221> NAME/KEY: DOMAIN
<222> LOCATION: (1) .. (6)
<223> OTHER INFORMATION: MF06 epitope

<400> SEQUENCE: 3

Asp Thr Arg Pro Ala Pro
 1               5

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: designed
      synthetical glycopeptide

<400> SEQUENCE: 4

Ala His Gly Val Thr Ser Ala Pro Asp Thr Arg Pro Ala Pro Gly Ser
 1               5                  10                  15

Thr Ala Pro Pro Ala
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: designed
      synthetical glycopeptide

<400> SEQUENCE: 5

His Gly Val Thr Ser Ala Pro Asp Thr Arg Pro Ala Pro Gly Ser Thr
 1               5                  10                  15

Ala Pro Pro Ala
            20

<210> SEQ ID NO 6
<211> LENGTH: 7
<212> TYPE: PRT
<213> ORGANISM: human
<220> FEATURE:
<221> NAME/KEY: DOMAIN
<222> LOCATION: (1) .. (7)
<223> OTHER INFORMATION: immunodominant motif of the epithelial mucin
      (MUC1)

<400> SEQUENCE: 6

Pro Asp Thr Arg Pro Ala Pro
 1               5
```